United States Patent [19]

Sultan

[11] Patent Number: 4,973,309
[45] Date of Patent: Nov. 27, 1990

[54] DISPOSABLE SYRINGE

[75] Inventor: Jean-Claude Sultan, Saint Jorioz, France

[73] Assignee: Microtechnic, Monaco

[21] Appl. No.: 457,769

[22] PCT Filed: Mar. 20, 1989

[86] PCT No.: PCT/FR89/00124
§ 371 Date: Nov. 21, 1989
§ 102(e) Date: Nov. 21, 1989

[87] PCT Pub. No.: WO89/09074
PCT Pub. Date: Oct. 5, 1989

[30] Foreign Application Priority Data

Mar. 21, 1988 [FR] France .................. 88 04118

[51] Int. Cl.⁵ ............................................. A61M 5/00
[52] U.S. Cl. ..................................... 604/110; 604/228
[58] Field of Search ................ 604/110, 218, 228, 187

[56] References Cited

U.S. PATENT DOCUMENTS 4,144,885 3/1979 Stait ..................................... 604/218
4,699,614 10/1987 Glazier ............................... 604/110
4,713,056 12/1987 Butterfield .......................... 604/110
4,883,466 11/1989 Glazier ............................... 604/110
4,915,692 4/1990 Verlier ............................ 604/228 X
4,932,941 6/1990 Min et al. ........................... 604/110

Primary Examiner—John D. Yasko
Attorney, Agent, or Firm—Browdy and Neimark

[57] ABSTRACT

A syringe comprising means making it possible to make the plunger (3) integral with the end (5) of the plunger stem (4) during the first filling, and to cause the disconnection between these elements during a refilling attempt.

According to the invention, the connecting means between the plunger (3) and the stem (4) comprise an intermediate memorization member (6) formed such that, during filling, it ensures that these two elements (3, 4) are integral while the injection, that is to say the pressure on the plunger stem (4), causes the displacement of the intermediate member (6) relative to the two elements (3, 4) so that the latter become detached upon any second filling attempt.

9 Claims, 2 Drawing Sheets

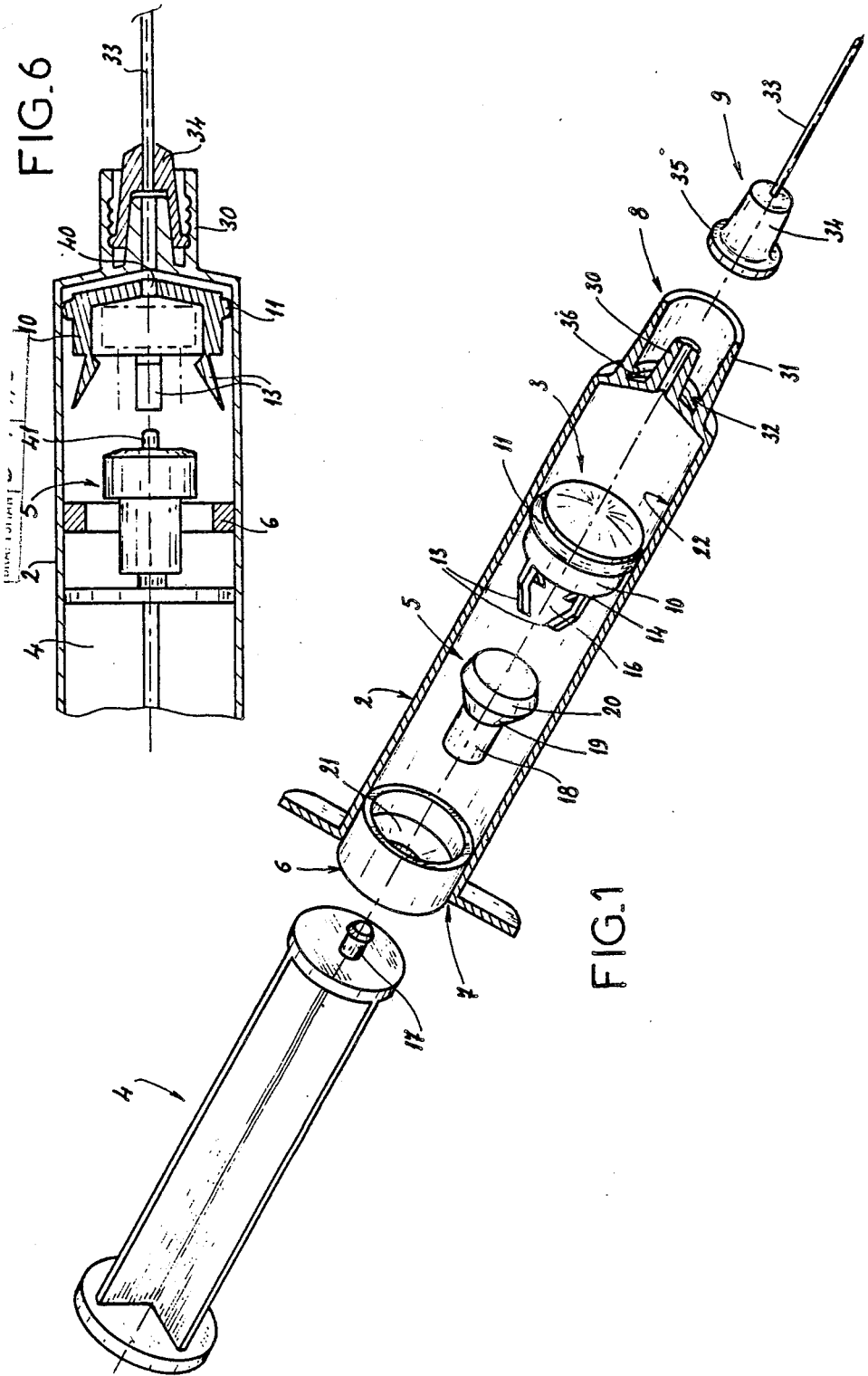

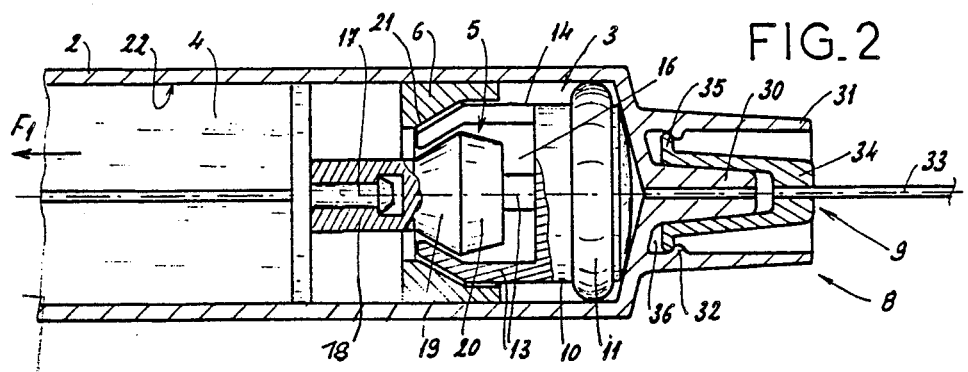
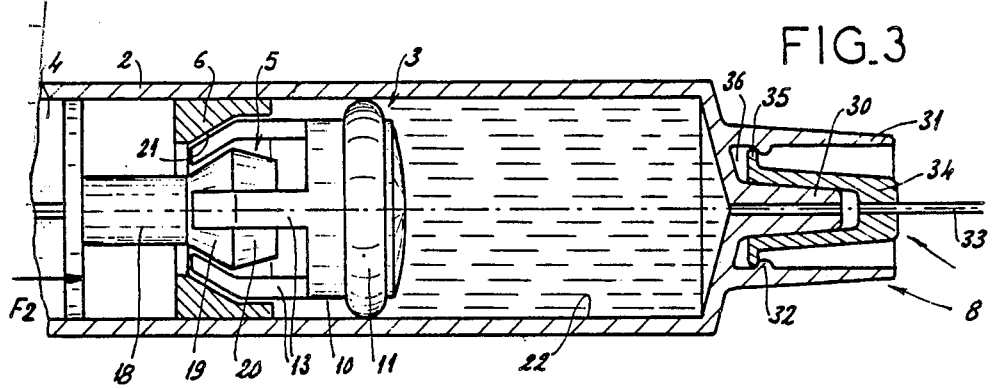
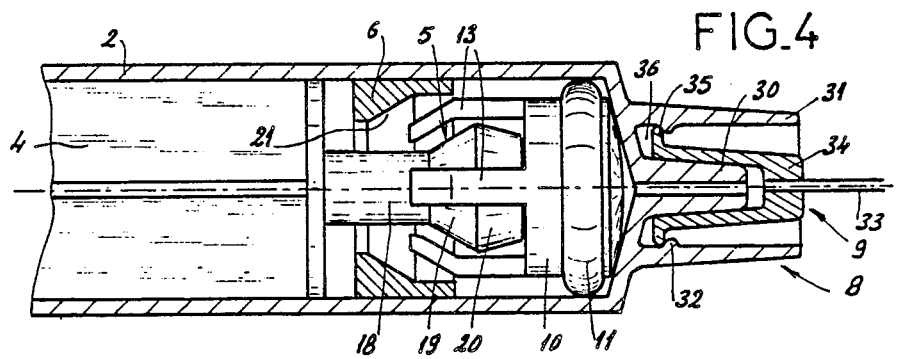
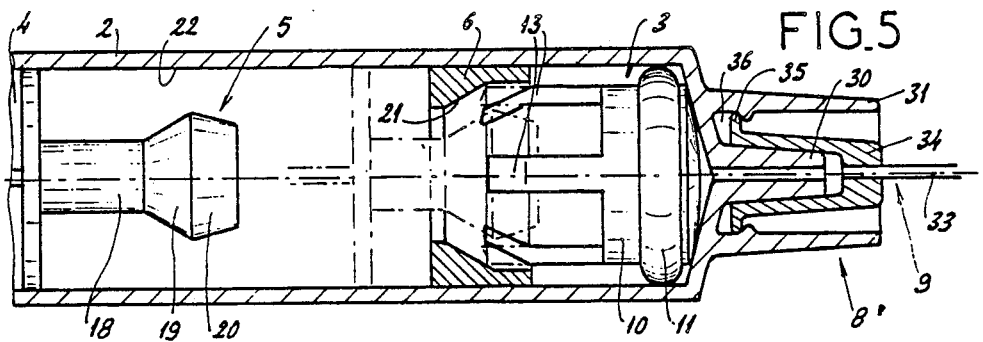

DISPOSABLE SYRINGE

The present invention relates to a disposable syringe of the type comprising a cylindrical body inside which moves a plunger which, with the end of the body comprising a needle support, sealingly defines an inner chamber of variable volume, the plunger being connected to the inner end of a plunger stem allowing same to be moved.

Syringes of such type are used in the medical field. They are supplied in sterile condition and are normally intended for once only use in order to avoid any risk of contamination. These syringes are generally sold with their plungers in the filling position, that is to say pushed to the end of the stroke inside the body.

However, these syringes have one major disadvantage: their technical structure does not make it possible to prevent a contaminated syringe from being reused. This phenomenom is especially common in risk groups such as drug addicts, where one syringe can be used for several injections for one person or for different persons. Furthermore, it is not unfeasible that repeated use could occur inadvertently in hospitals.

Now, such practices create conditions which are very favourable for the propagation of very serious infectious diseases such as AIDS or hepatitis B.

In order to overcome these drawbacks, the idea was conceived to make disposable syringes.

Document EP-A-0 229 017 relates to a syringe of this type in which the plunger stem is detachably coupled to the plunger so as to ensure that the stem and the plunger are disconnected when a pulling action is exerted on the stem after the first injection. To this end, the plunger is extended on the side of the stem by a conical part followed by a cylindrical part and a disk having a peripheral flange. The plunger stem itself is provided with several tabs which, acting on the edges of the disk like a clamp, have areas of reduced thickness or break lines at the point of connection to the stem. When the injection is completed, the tabs come to rest on the conical part and spread apart, which results in that they break or become sufficiently deformed so as to be no longer able to grip the edge of the disk.

However, this solution is not satisfactory. In fact, the force acting on the gripping tabs is variable depending on several parameters: the viscosity, the diameter of the needle and the injection speed. A low viscosity of the fluid, a low injection speed, or a large diameter of the needle do not generate sufficient resistance to cause breaking of the tabs during the injection. The reliability of thys syringe is therefore risky. Besides, it is possible before the first use to dismantle the syringe and to block the tabs by surrounding them, for example with adhesive tape, which makes it impossible subsequently to spread them apart and thus to break them.

The essential purpose of the present invention is to overcome this drawback by providing a disposable syringe which allows only a single injection by preventing in a reliable and irreparable manner that the inner chamber of the syringe is filled for a second time.

To this end, this syringe of the type comprising a cylindrical hollow body inside which moves a plunger which, with the end of the body comprising a needle support, sealingly defines an inner chamber of variable volume, the plunger being connected to the inner end of a plunger stem allowing same to be moved, and means which make it possible, on the one hand, to make the plunger integral with the inner end of the plunger stem during the first filling of the inner chamber and, on the other hand, to cause the disconnection of the plunger from the inner end of the plunger stem upon any attempt to refill the inner chamber, is characterized in that the connecting means between the plunger and the stem comprise an intermediate memorization member which is formed such that, during filling, it ensures the integration between these two elements, while the injection, that is to say the pressure on the plunger stem, causes the intermediate member to be displaced relative to these two elements so that they will come apart upon any second filling attempt.

According to a preferred embodiment of the invention, the inner end of the plunger stem comprises a ferrule having an axis corresponding to that of the body and having at least one zone in the shape of a truncated cone, the largest diameter of which is situated on the side of the plunger, said zone being disposed, upon assembly, in a hollow extension of the plunger which is turned on the side of the stem so as to form a wedge locking this extension against the memorization member, constituted by a ring whose periphery rests against the wall of the body.

In order to facilitate the assembly of the syringe and to optimize its operation, the truncated cone-shaped zone of the ferrule of the stem is extended, on the one hand, by a cylindrical part fixed on the plunger stem and, on the other hand, on the side of its free end, by a converging part having the shape of a truncated cone.

According to an interesting feature of the invention, the hollow extension of the plunger is constituted by four tabs extending from the periphery of the latter, each comprising, starting from the plunger, a part parallel to the axis of the syringe extended by an inwardly inclined part, the outer and inner faces of each tab being intended to come into contact, respectively, with the inner face of the memorization ring and the truncated cone-shaped zone of the ferrule.

In order to allow the memorization ring to become displaced during the injection, the length of the converging part of the ferrule is less than that of the part of each tab of the plunger which is parallel to the axis of the syringe.

The ferrule is advantageously fixed to the end of the stem by clamping onto a teat integral therewith.

Upon the first filling of the syringe, the extension of the plunger is wedged between the memorization ring of the ferrule of the stem of the syringe.

The conical part of the ferrule thus ensures that the plunger is driven in the direction of the outlet of the stem.

During the actual injection, which takes place by pushing on the stem, a displacement occurs between the plunger and the memorization ring, such that the latter no longer clamps the tabs forming the extension of the plunger. The result is that, if a pulling force is exerted on the stem, in order to refill the syringe, the tabs which are no longer held by the memorization ring allow the ferrule to escape, so that the plunger can no longer be retracted.

In order to ensure even more reliably that the syringe is used only once, the needle support located at one of the ends of the body advantageously has the form of a tube with a diameter which is less than that of the body connecting the inner chamber of the syringe to the outside and intended to receive, on its outer surface, a cap having a complementary shape supporting the hollow metal part of the needle at one of its ends, the tube being disposed inside a cylindrical skirt integral with the body by one of its ends and having a length greater than that of the tube, such that, when the cap is fitted onto the tube, the skirt completely envelops this cap.

This arrangement prevents the retraction of the needle after it has been placed on the support of the body, because it is difficult and dangerous to manipulate it by holding it by its fine metal part, which part is the only part that can be gripped.

In order to make sure that the mounting of the needle cannot be violated, the cap is advantageously provided with an annular rim capable of irreversibly engaging into a recess of complementary shape provided on the skirt or on the tube.

In any event, the invention will be better understood and its advantages will be apparent from the following description with reference to the accompanying diagrammatic drawing which shows, by way of non-limiting examples, two embodiments of the disposable syringe.

FIG. 1 is an exploded perspective view,

FIG. 2 is a longitudinal sectional view before filling,

FIG. 3 is a longitudinal sectional view after filling,

FIG. 4 is a longitudinal sectional view after the injection,

FIG. 5 is a longitudinal sectional view taken during a second filling attempt,

FIG. 6 is a partial view, in longitudinal section, of the front part of a variant embodiment of this syringe.

FIG. 1 shows the syringe 1 according to the invention. It is formed by a cylindrical hollow syringe body 2, made for example of plastic or of glass, seen in longitudinal section, inside which are mounted a plunger 3, a plunger stem 4 intended to be connected to a ferrule 5 and a memorization ring 6. These elements are introduced through the open end 7 of the body of the syringe 2, its other end being designed as a support 8 for a needle 9.

As is also shown in FIGS. 2 to 5, the piston 3 which is made, for example, of a synthetic material, is formed by a cylindrical part 10 with a diameter which is smaller than that of the body 2 provided with an O-ring 11 fixed in an annular groove not specifically marked. This O-ring 11 makes it possible to define, with the end 8 of the body of the syringe 2, a sealed inner chamber 12.

The cylindrical part 10 of the plunger is extended in the direction of the plunger stem 4 by four identical tabs 13. These tabs 13 extend from the periphery of the cylindrical part 10 and are offset at an angle of 90° relative to each other. Each tab 13 of rectangular cross-section comprises, starting from the plunger 3, a part parallel to the axis of the syringe 1 ending in an inwardly inclined part, the outer face of its part parallel to the axis of the syringe 1 being designated by reference numeral 14 in the drawing. Inside the hollow extension 16 of the plunger 3, defined by the four tabs 13, there is disposed the ferrule 5 forming the inner end of the plunger stem 4. This ferrule 5, having an axis corresponding to that of the body 2, is fastened on the stem 4 through a teat 17 integral therewith and being clamped in a cavity of complementary shape made in a cylindrical part 18 of the ferrule 5. This cylindrical part is extended by an area 19 having the shape of a truncated cone, the largest diameter of which is found on the side of the plunger, and ends in a converging part 20 having the shape of a truncated cone, the length of which is shorter than that of the part parallel to the axis of the syringe 1 of each tab 13.

The ferrule 5 of the stem 4 and the plunger 3 are connected through the memorization ring 6.

In fact, as appears from FIGS. 2 and 3, the outer face 14 and the inner face of each tab 13 are held in contact, respectively, with the inner face 21 of the memorization ring 6 and the truncated cone-shaped zone 19 of the ferrule 5. The periphery of the memorization ring 6 in turn rests against the wall 22 of the body 2.

The ferrule 5, by means of its truncated cone-shaped zone 19, is therefore designed as a wedge locking the tabs 13 against the memorization ring 6. The inner face 21 of the ring 6 and the outer faces 14 of the tabs 13 are of complementary shape.

As regards the support 8 for the needle 9, it is formed by a tube 30 with a diameter which is less than that of the body 2. This tube 30 connects the inner chamber 12 with the outside. It has an axis corresponding to that of the body 2 and is disposed inside a cylindrical hollow skirt 31 which is integral with the body 2 through one of its ends. This skirt 31 has a diameter and a length which are greater than those of the tube 30. Furthermore it has an annular rib 32 on the inner face of its wall, in the vicinity of the body.

The needle 9 is formed by a hollow metal part 33 which is integral through one of its ends with a cap 34 of plastic material intended to be fitted onto the tube 30. This cap 34 has an annular rim 35 over the circumference of its open end.

As can be seen in FIGS. 2 to 5, after the cap 34 has been fitted onto the tube 30, the annular rim 35 is locked, in a recess 36 of the skirt 31, by the annular rib 32, thus preventing the retraction of the needle 9.

The operation of the syringe 1 according to the invention is illustrated by FIGS. 2 to 5.

FIG. 2 shows the syringe 1 assembled and ready for use. The plunger 3 is pushed to the end of its stroke into the hollow body 2. The inner chamber 12 thus has a volume which is reduced to its minimum.

The first and only filling of this chamber 12 is performed by dipping the fine metal part 33 of the needle 9 into the liquid to be injected and by subsequently exerting a pulling force in the direction of arrow F1 (FIG. 2) on the plunger stem 4.

The plunger 3, whose extensions of the tabs 13 are wedged between the memorization ring 6 and the truncated cone-shaped zone 19 of the ferrule 5, is moved along by the stem 4. The wedging effect, further accentuated by the pulling action on the stem 4 of the extensions 13 between the ferrule 5 and the memorization ring 6, implies that the latter is also moved along in translation with the plunger 3 and the stem 4. The depression thus created leads the liquid to be injected into the inner chamber 12 which is filled to the desired volume. FIG. 3 illustrates this situation.

All that remains to be done is to proceed with the injection. To this end, pressure is exerted on the plunger stem 4 in the direction of arrow F2 (FIG. 3).

The free end of the ferrule 5 then comes into contact with the plunger 3 and moves it in translation in the direction of the bottom of the body 2 thus forcing the liquid to be injected through the needle 9. The displacement of the ferrule 5 relative to the plunger 3 releases the extensions of the tabs 13 from the memorization ring 6. As a result, the latter is displaced relative to the plunger 3 and to the tabs 13 and takes up the position shown in FIG. 4.

The result, as shown in FIG. 5, is that, when someone wants to refill the syringe, by exerting a pulling action on the stem 4, the tabs 13, released from the hold by the memorization ring 6, are elastically deformed and allow the ferrule 5 to escape, as is illustrated in dash-and-dot lines in FIG. 5.

Hence, the plunger 3 remains in its position inside the body of the syringe 2 and the ferrule 5 is completely detached from the plunger/ring assembly without being able to be moved back into the position which it occupied in FIG. 2.

A second filling of the inner chamber 12 is then impossible, which makes the syringe 1 unusable and thus prevents any risk of contamination.

In this example, safety is further improved by the fact that the connection between the needle and its support cannot be violated.

In the embodiment shown in FIG. 6, the plunger 10 comprises a central passage orifice 40 into which a pin 41 integral with the ferrule 5 is intended to be engaged. The engagement of the pin 41 into the orifice 40 ensures that the latter is tightly sealed. After the first use of the syringe and the disconnection of the ferrule 5 and the plunger 10, the orifice 40 is open, so that it is impossible to ensure the return movement of the plunger by the injection of fluid under pressure from the needle. This further enhances the disposable character of this syringe.

Obviously, the invention is not limited to the embodiment of the syringe described hereinabove by way of example; to the contrary, it embraces all variant embodiments.

Thus, the syringe could comprise a conventional needle support such as those currently existing, which are formed by a tube onto which the cap supporting the metal part of the needle is fitted, while the memorization ring could be continuous or non-continuous. In the latter case, it would have a slit which would give it a certain degree of elasticity facilitating its introduction into the syringe body, or the extension of the plunger could be formed by a different number of tabs or by a continuous and deformable skirt.

I claim:

1. A disposable syringe, of the type comprising a cylindrical hollow body (2) inside which moves a plunger (3) which, with the end of the body comprising a support (8) for a needle (9), sealingly defines an inner chamber (12) of variable volume, the plunger (3) being connected to the inner end (5) of a plunger stem (4) allowing same to be moved, and means (6, 13) making it possible, on the one hand, to make the plunger (3) integral with the inner end (5) of the plunger stem (4) during the first filling of the inner chamber (12) and, on the other hand, to cause the disconnection of the plunger (3) from the inner end (5) of the plunger stem (4) during any attempt to refill the inner chamber (12), characterized in that the connecting means between the plunger (3) and the stem (4) comprise an intermediate memorization ring (6) formed such that it ensures, during filling, that these two elements (3, 4) are integral, while the injection, that is to say the pressure on the plunger stem (4), causes the intermediate member (6) to be displaced relative to the two elements (3, 4) so that the latter become detached during any second filling attempt.

2. A syringe according to claim 1, characterized in that the inner end of the plunger stem (4) comprises a ferrule (5) having an axis corresponding to that of the body (2) and having at least one zone (19) having the shape of a truncated cone, the largest diameter of which is situated on the side of the plunger (3), this truncated cone-shaped zone (19) being disposed, upon assembly, in a hollow extension (16) of the plunger (3) turned on the side of the stem (4) so as to form a wedge locking this extension (16) against the memorization member constituted by a ring (6) whose periphery rests against the wall (22) of the body (2).

3. A syringe according to claim 2, characterized in that the truncated cone-shaped zone (19) of the ferrule (5) of the stem (4) is extended, on the one hand, by a cylindrical part (18) fixed on the plunger stem (4) and, on the other hand, on the side of its free end, by a converging part (20) having the shape of a truncated cone.

4. A syringe according to claim 2, characterized in that the hollow extension (16) of the plunger (3) is formed by four tabs (13) extending from the periphery of the latter, offset at an angle of 90° relative to each other, each comprising, starting from the plunger (3), a part parallel to the axis of the syringe (1) and extended by an inwardly inclined part, the outer face (14) and inner face of each tab (13) being intended to come into contact, respectively, with the inner face (21) of the memorization ring (6) and the truncated cone-shaped zone (19) of the ferrule (5).

5. A syringe according to claim 3, characterized in that the length of the converging part (20) of the ferrule (5) is shorter than that of the part of each tab of the plunger (3) which is parallel to the axis of the syringe (1).

6. A syringe according to claim 2, characterized in that the ferrule (5) is fastened to the end of the stem (4) by clamping onto a teat (17) integral therewith.

7. A syringe according to claim 1, characterized in that the support (8) of the needle (9) located at one of the ends of the body (2) is in the form of a tube (30) having a diameter which is smaller than that of the body (2) connecting the inner chamber (12) of the syringe (1) to the outside and intended to receive, on its outer face, a cap (34) of complementary shape supporting the metal hollow part (33) of the needle (9) at one of its ends, the tube (30) being disposed inside a cylindrical hollow skirt (31) which is integral with the body (2) through one of its ends and which has a length greater than that of the tube (30) so that, when the cap (34) is fitted onto the tube, the skirt (31) completely envelops this cap (34).

8. A syringe according to claim 7, characterized in that the cap (34) is provided with an annular rim (35) capable of being irreversibly engaged inside a housing (36) of complementary shape provided on the skirt (31) or on the tube (30).

9. A syringe according to claim 1, characterized in that the plunger (10) comprises at least one passage orifice (40), intended to be closed by a pin (41) which is integral with the ferrule (5) when the plunger and the ferrule are integral with each other.

* * * * *